(12) United States Patent
Holker et al.

(10) Patent No.: US 7,003,336 B2
(45) Date of Patent: Feb. 21, 2006

(54) ANALYTE SENSOR METHOD OF MAKING THE SAME

(75) Inventors: James D. Holker, Alta Loma, CA (US); Guillermo A. Calle, Simi Valley, CA (US); Kevin D. Branch, Northridge, CA (US); John J. Mastrototaro, Los Angeles, CA (US); William P. Van Antwerp, Valencia, CA (US); Nannette Van Antwerp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 323 days.

(21) Appl. No.: 09/779,282

(22) Filed: Feb. 8, 2001

(65) Prior Publication Data

US 2002/0032374 A1 Mar. 14, 2002

Related U.S. Application Data

(63) Continuation of application No. 09/502,444, filed on Feb. 11, 2000, now abandoned, which is a continuation of application No. 09/502,204, filed on Feb. 10, 2000, now Pat. No. 6,484,045.

(51) Int. Cl.
*B65D 85/38* (2006.01)
*A61B 5/05* (2006.01)
*A61B 5/04* (2006.01)

(52) U.S. Cl. ............... 600/316; 600/347; 600/391; 206/305

(58) Field of Classification Search ........ 600/316–391, 600/309, 392; 435/25; 156/268; 206/305; 604/272, 174, 503, 504, 44, 48, 180
See application file for complete search history.

(56) References Cited

U.S. PATENT DOCUMENTS

| 3,224,433 | A | * | 12/1965 | Von Dalebor | ............... 600/361 |
| 3,224,436 | A | * | 12/1965 | Von Dalebor | ............... 600/361 |
| 4,543,953 | A | * | 10/1985 | Slocum et al. | ................ 607/32 |

(Continued)

FOREIGN PATENT DOCUMENTS

WO        WO 98/56293        12/1998

(Continued)

OTHER PUBLICATIONS

Koudelka, M. et al., "Planar Amperometric Enzyme-Based Glucose Microelectrode", *Sensors and Actuators*, 18 (Elsevier Sequoia, The Netherlands—1989), pp. 157-165.

(Continued)

*Primary Examiner*—Kevin C. Sipmons
*Assistant Examiner*—Roz Maiorino
(74) *Attorney, Agent, or Firm*—Medtronic MiniMed, Inc.

(57) ABSTRACT

A sensor and method of making the same for implantation in a body that includes a substrate with notches cut in the substrate to form a necked down region in the substrate; and at least one sensor electrode formed from one or more conductive layers. Preferably, the thickness of the substrate ranges from approximately 25µ to 350µ, but the thickness of the substrate can range from 5µ to 750µ. The sensor may be incorporated in to a sensor assembly includes a slotted needle having a slot. The notches creating the necked down region allow the substrate to slide into the slotted needle, which that has the slot narrow enough to permit passage of the necked down region. However, a non-necked down region of the substrate is prevented from pulling out of the slotted needle through the slot. The slot of the slotted needle may also permit the necked down region of the substrate to slide down the slot.

14 Claims, 11 Drawing Sheets

U.S. PATENT DOCUMENTS

| | | | |
|---|---|---|---|
| 5,108,819 A | 4/1992 | Heller et al. | 428/195 |
| 5,165,407 A | 11/1992 | Wilson et al. | 128/635 |
| 5,299,571 A | 4/1994 | Mastrototaro | 128/634 |
| 5,322,063 A | 6/1994 | Allen et al. | 128/635 |
| 5,390,671 A * | 2/1995 | Lord et al. | 600/347 |
| 5,391,250 A * | 2/1995 | Cheney et al. | 156/268 |
| 5,411,647 A | 5/1995 | Johnson et al. | 204/153.1 |
| 5,586,553 A * | 12/1996 | Halili et al. | 600/316 |
| 5,777,060 A | 7/1998 | Van Antwerp | 528/28 |
| 5,786,439 A | 7/1998 | Van Antwerp et al. | 528/77 |
| 5,951,521 A * | 9/1999 | Mastrototaro et al. | 604/174 |
| 6,032,064 A * | 2/2000 | Devlin et al. | 600/383 |
| 6,103,033 A | 8/2000 | Say et al. | 156/73.1 |
| 6,162,611 A | 12/2000 | Heller et al. | 435/14 |
| 6,259,937 B1 * | 7/2001 | Schulman et al. | 600/345 |
| 6,360,888 B1 * | 3/2002 | McIvor et al. | 206/305 |
| 6,461,496 B1 * | 10/2002 | Feldman et al. | 205/777.5 |
| 6,484,045 B1 * | 11/2002 | Holker et al. | 600/345 |
| 6,498,043 B1 * | 12/2002 | Schulman et al. | 438/1 |
| 6,564,079 B1 * | 5/2003 | Cory et al. | 600/393 |

FOREIGN PATENT DOCUMENTS

| | | |
|---|---|---|
| WO | WO99/45375 | 9/1999 |
| WO | WO 99/45387 | 9/1999 |
| WO | WO 99/56613 | 11/1999 |

OTHER PUBLICATIONS

Koudelka, M. et al., "In-vivo Behaviour of Hypodermically Implanted Microfabricated Glucose Sensors", *Biosensors & Bioelectronics* 6 (Elsevier Science Publishers Ltd., England—1991), pp. 31-36.

Mastrototaro, John M. et al., "An electroenzymatic glucose sensor fabricated on a flexible substrate", *Sensors and Actuators B. 5* (Elsevier Sequoia—1991), pp. 139-144.

Urban, G. et al., "Miniaturized multi-enzyme biosensors integrated with pH sensors on flexible polymer carriers for in vivo applications", *Biosensors & Bioelectronics 7* (Elsevier Science Publishers Ltd.—1992), pp. 733-739.

"3M Specifications and Design Guidelines, Microflex circuits for IC Interconnect Solutions," pp. 1-32 (the entire document), 1997 (3M Electronic Products Division, Austin TX).

"3M Offers More Solutions for the Semiconductor Industry" the entire document, 1997 (3M Electronic Products Division, Austin TX).

"Microflex Solutions from 3M", the entire document, 1996 (3M Electronic Products Division, Austin TX).

"Micron Wide Conductors and Space on . . . PZT, Alumina, Glass and Flexible Material" 1 page, no date (Metrigraphics, Wilmington, MA).

"Flexible circuits at Extreme Density", 8 unnumbered pages of various dates (Metrigraphics, Wilmington, MA).

"Metrigraphics Ion Beam Etching Capability", 1 page, no date (Metrigraphics Wilmington, MA).

* cited by examiner

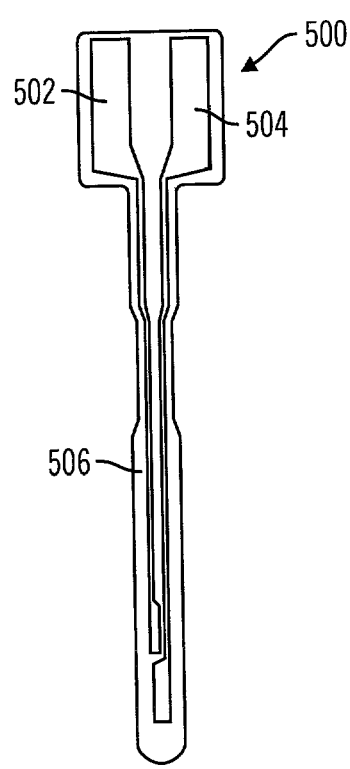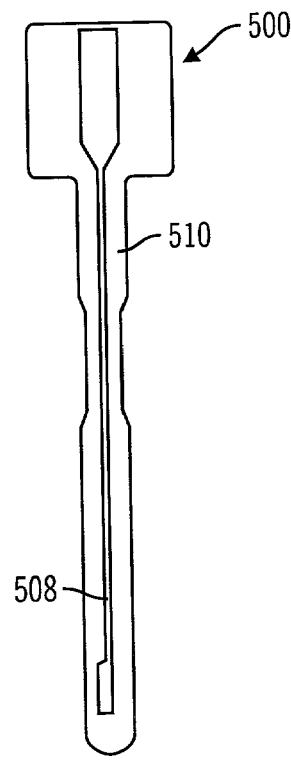
FIG. 30a  FIG. 30b
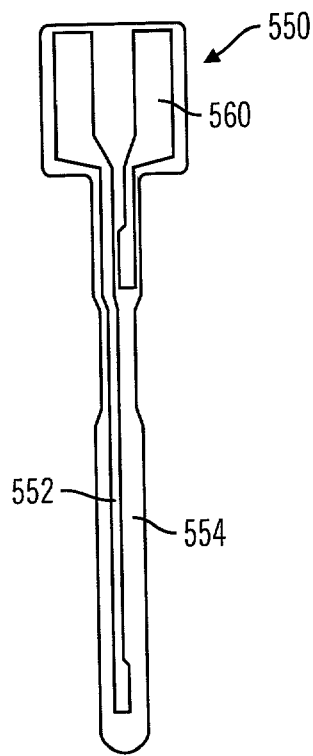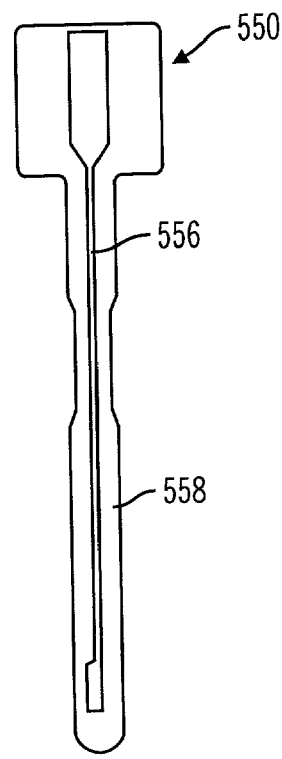
FIG. 31a  FIG. 31b

ANALYTE SENSOR METHOD OF MAKING THE SAME

RELATED APPLICATIONS

This application is a continuation of U.S. patent application Ser. No. 09/502,444, filed Feb. 11, 2000, now abandoned which is a continuation of U.S. patent application Ser. No. 09/502,204 filed Feb. 10, 2000 now U.S. Pat. No. 6,484,045, both of which are specifically incorporated by reference.

FIELD OF THE INVENTION

The present invention relates to methods for producing sensors that include flexible substrates and one or more sensor electrodes, and in particular embodiments to sensor sets including such sensors.

BACKGROUND OF THE INVENTION

Methods for producing sensors, particularly sensors useful in sensor sets for the determination of a body characteristic such as blood glucose levels, are known. Examples of such sensors, sensor sets and methods for production thereof are described, e.g., in commonly assigned U.S. Pat. No. 5,390,691; No. 5,391,250; No. 5,482,473; No. 5,299,571; No. 5,586,553; and No. 5,568,806, each of which is incorporated in its entirety herein by reference.

Certain known methods, such as that described in U.S. Pat. No. 5,391,250, form the sensor electrodes by an etching process. Etching processes are often multi-step procedures that can be time-consuming and expensive. Accordingly, a need exists for a simplified process for producing sensors.

Alternative methods described in PCT/US99/03781, published Sep. 10, 1999 and based on U.S. patent application Ser. No. 09/034,422, form sensor electrodes by, for example, first forming a channel in a substrate, which can be a continuous web, and then depositing conductive material in the channel to form the electrode.

A need also exists for an improved process that enables continuous formation of sensors.

SUMMARY OF THE PREFERRED EMBODIMENTS

It is an object of an embodiment of the present invention to provide an improved sensor and method of making the same, which obviates for practical purposes, the above mentioned limitations.

According to an embodiment of the invention, a sensor and a method of making the same for implantation in a body includes a substrate with notches cut in the substrate to form a necked down region in the substrate; and at least one sensor electrode formed from one or more conductive layers. In preferred embodiments, the thickness of the substrate ranges from approximately $25\mu$ to $350\mu$, but the thickness of the substrate can range from $5\mu$ to $750\mu$. In particular embodiments, a sensor assembly includes the sensor and a slotted needle having a slot. The notches creating the necked down region allow the substrate to slide into the slotted needle, which that has the slot narrow enough to permit passage of the necked down region. However, a non-necked down region of the substrate is prevented from pulling out of the slotted needle through the slot. In other embodiments, the slot of the slotted needle permits the necked down region of the substrate to slide down the slot.

In further embodiments, a width of the substrate in the non-necked down portion is sized to fit within a slotted needle having a diameter smaller than 21 gauge, 22 gauge, 23 gauge, 24 gauge or the like. In additional embodiments, at least one of the at least one sensor electrode is formed on a first surface of the substrate. In alternative embodiments, all of the at least one sensor electrode are only formed on the first surface. In other alternative embodiments, at least another one of the at least one sensor electrodes is formed on a second surface of the substrate. In still other alternative embodiments, a third one of the at least one sensor electrode is a reference electrode configured to contact a skin surface.

In yet another embodiment, sensors are formed as a part of sensor set that includes a sensor, mounting base and insertion needle. The mounting base adapted for mounting onto a patient's skin. The insertion needle is carried by the mounting base to protrude from the mounting base and has at least a portion of the sensor nested within the insertion needle. The insertion needle defines a longitudinally extending slot along one side to permit sliding withdrawal of the insertion needle from the mounting base and the nested portion of the sensor. The slot is also configured to accept the necked down region of the substrate.

In accordance with one aspect of the present invention, there is provided a method of making a sensor that includes the steps of providing a pre-formed self-supporting flexible substrate; sputter-depositing a metal layer on the substrate; etching the sputter-deposited metal layers to form a sensor electrode having a proximal segment and a distal segment; plating a metal layer on the sensor electrode; and separating the sensor electrode and at least a portion of the substrate underlying the sensor electrode from the remainder of the substrate. Preferably, the substrate is comprised of a polymeric material, such as a polyimide, and in more particular embodiments, the substrate is supplied in the form of a continuous web.

In particular embodiments, a plurality of metal layers are sequentially sputter-deposited, and the plated layer is formed on the uppermost sputter-deposited layer of the sensor electrode. Preferably, the sputter-deposited metal layers are comprised of different metals, such as layers of chromium and copper.

According to another preferred embodiment, prior to the sputter-deposition step a layer of a material that promotes adhesion between the sputter-deposited metal layer and the substrate is deposited on the substrate. In other embodiments, during the plating step, a layer of copper or a layer of gold is plated on the sensor electrode. Alternatively, a plurality of layers are sequentially plated on the sensor electrode.

In other embodiments, prior to the separation step, the sensor electrode is provided with a coating, such as a coating of a polymeric material, and/or a biocompatible polymeric material. Preferably, the coating is subsequently removed from the proximal segment and the distal segment of the sensor electrode. In further embodiments, the coating is removed from the distal segment of the sensor electrode and the distal segment is subsequently provided with an electrode chemistry. In other embodiments, the sensor electrode is provided with a membrane after the distal segment is provided with the electrode chemistry.

According to a particular embodiments, a plurality of sprocket holes are formed in the substrate adjacent to the sensor electrode. Also, in preferred embodiments, the step of removing the sensor is carried out using a laser.

In preferred embodiments, the substrate has an upper surface and a lower surface. The sensor electrode is formed on the upper surface, and after the etching step a bead is formed on at least one of the lower surface and the sensor electrode. The bead is formed, according to one particular embodiment, below and in alignment with the sensor electrode. According to another particular embodiment, a first bead is formed on the lower surface of the substrate and a second bead is formed on the sensor electrode. Preferably, the bead is formed using a liquid polymer, and is formed using a molding process.

In accordance with another embodiment of the present invention, a method of making a sensor includes the steps of providing a pre-formed self-supporting flexible substrate; sequentially sputter-depositing a plurality of metal layers on the substrate, the plurality of layers including an uppermost layer; plating a metal layer on the uppermost sputter-deposited metal layer; etching the plated and sputter-deposited metal layers to form a sensor electrode having a proximal segment and a distal segment; sequentially plating first and second metal layers on the sensor electrode; coating the sensor electrode with a polymeric material; forming at least one opening in the coating; and separating the sensor electrode and at least a portion of the substrate underlying the sensor electrode from the remainder of the substrate.

In preferred embodiments, layers of chromium and copper are sequentially sputter-deposited. Preferably, at least one layer of copper is plated on the sputtered layer(s) prior to etching, and layers of copper and gold are sequentially plated after the etching step.

In accordance with an additional embodiment of the present invention, a method of making a sensor includes the steps of providing a pre-formed self-supporting flexible substrate; sputter-depositing at least one metal layer on the substrate; etching the at least one metal layer to form a sensor electrode having a proximal segment and a distal segment; and separating the sensor electrode and at least a portion of the substrate underlying the sensor electrode from the remainder of the substrate.

In accordance with still another embodiment of the present invention, a method of making a sensor includes the steps of providing a substrate having an upper surface and a lower surface; sputter-depositing at least one metal layer on at least one surface of the substrate; etching the at least one metal layer to form a sensor electrode having first and second edges, a proximal segment and a distal segment; forming a bead on at least one of the upper surface and the lower surface of the substrate; and separating the sensor electrode and the portion of the substrate underlying the sensor electrode from the remainder of the substrate.

In preferred embodiments, the sensor electrode is formed on one of the upper and lower surfaces of the substrate and the bead is formed on the other surface of the substrate. In a further embodiments, the bead is formed on the substrate beneath the sensor electrode.

According to particular embodiments, the bead is formed by forming a perforation in the substrate adjacent to the first and second edges of the sensor electrode; securing the lower surface of the substrate to a mold, the mold having a channel that extends beneath the sensor electrode; flowing a liquid polymer over the upper surface of the substrate and through the perforations into the channel until the polymer beads on the upper surface of the substrate and covers at least a portion of the sensor electrode; curing the liquid polymer; and removing the substrate from the mold. In further embodiments, the perforations on each side of the sensor electrode include at least one perforation gap. The liquid polymer that flows over the sensor electrode does not cover the portion of the sensor electrode between the perforation gaps. The perforations on each side of the sensor electrode may include a plurality of perforation gaps. In still other embodiments, each perforation has a perforation gap adjacent to at least one of the proximal and distal segments of the sensor electrode. In a preferred embodiment, the distal segment is provided with an electrode chemistry.

According to yet another embodiment of the present invention, a method of making a sensor includes the steps of: providing a substrate having an upper surface and a lower surface; forming at least one channel in at least one of the upper and lower surfaces of the substrate; disposing a conductive material in the at least one channel to form at least one electrode; and forming a bead on at least one of the upper and lower surfaces of the substrate to produce a sensor.

According to a further embodiment of the present invention, a method of making a sensor includes the steps of: providing a substrate having an upper surface and a lower surface; disposing a conductive material on at least one of the upper and lower surfaces of the substrate by non-impact printing to form at least one electrode; and forming a bead on at least one of the upper and lower surfaces of the substrate to produce a sensor.

According to yet a further embodiment of the present invention, a method of making a sensor includes the steps of: providing a substrate having an upper surface and a lower surface; providing a film or sheet comprising a conductive material; transferring the conductive material from the film or sheet to the substrate to form at least one electrode; and forming a bead on at least one of the upper and lower surfaces of the substrate to produce a sensor.

According to still a further embodiment of the present invention, a method of making a sensor includes the steps of: providing a substrate having an upper surface and a lower surface; depositing at least one layer of a metal on the upper surface of the flexible substrate; etching the at least one metal layer to form a sensor electrode having first and second edges, a proximal segment and a distal segment; forming a perforation in the substrate adjacent to the first and second edges of the sensor electrode; securing the lower surface of the substrate to a mold, the mold having a channel that extends below the metal layer; flowing a liquid polymer over the upper surface of the substrate and through the perforations into the channel until the polymer covers the upper surface of the substrate and at least a portion of the sensor electrode; curing the liquid polymer; removing the substrate from the mold; and removing the sensor electrode, the cured polymer and the portion of the substrate between the first and second perforations by separating the substrate adjacent to the perforations.

According to another embodiment of the present invention, a method of making a sensor includes the steps of: providing a substrate; forming a bead on a surface of the substrate; forming a sensor electrode on the substrate; and separating the bead, the sensor electrode and at least a portion of the substrate between the bead and the sensor electrode from the remainder of the substrate.

According to yet another embodiment of the present invention, a method of making a sensor includes the steps of: providing a substrate; forming a sensor electrode on a surface of the substrate; forming a bead on the substrate; and separating the bead, the sensor electrode and at least a portion of the substrate between the bead and the sensor electrode from the remainder of the substrate.

In accordance with further embodiments of the present invention, sensors produced according to the foregoing methods are also provided. In accordance with other embodiments of the present invention, sensor sets that include sensors, as described herein, together with appropriate mounting bases and insertion needles are provided. In additional embodiments, the sensor sets include cannula in which portions of the sensor are disposed and which in turn are at least partially disposed within the insertion needles. In other embodiments, the sensor includes a bead, which is at least partially nested within the insertion needle, obviating the need for a cannula.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

A detailed description of embodiments of the invention will be made with reference to the accompanying drawings, wherein like numerals designate corresponding parts in the several figures.

FIGS. 1–4 illustrate an embodiment of a first method according to the invention in which a substrate, illustrated as a flexible tape supplied from a reel, is provided with at least one metal layer deposited on its upper surface, an optional plating of one or more metal layers, followed by an etching step to form one or more sensor electrodes, and an optional plating of one or more additional layers, after which the metal layer(s) and the underlying portion of the substrate are subsequently separated from the remainder of the substrate;

FIG. 1 is an illustration of a reel and tape used to provide a substrate for use in the methods in accordance with embodiments of the present invention;

FIG. 4 is a cross-sectional view of the sensor after being separated from the remainder of the substrate;

FIGS. 15–21 illustrate another alternative embodiment of a method according to the invention, wherein FIG. 16 is a transverse section illustrating formation of perforations on either side of the metal layer of FIG. 15a, FIG. 17 is a transverse section showing the position of the substrate of FIG. 16 in relation to a mold having defined therein a channel;

FIG. 19 is a transverse section illustrating the curing of the liquid polymer;

FIG. 20 is a side section illustrating disengagement of the mold from the substrate and the cured polymer;

FIG. 21 is a transverse section along the lines 21—21 of FIG. 20 showing separation of the completed sensor from the remainder of the substrate;

FIGS. 23–25 illustrate alternative methods for producing sensors, after which beads are provided in accordance with the methods described herein, in which

FIGS. 30(a) and (b) are plan views of an alternative embodiment of the sensor shown in FIGS. 26–29.

FIGS. 31(a) and (b) are plan views of another alternative embodiment of the sensor shown in FIGS. 26–29.

DETAILED DESCRIPTION OF THE PREFERRED EMBODIMENTS

Figure 1:
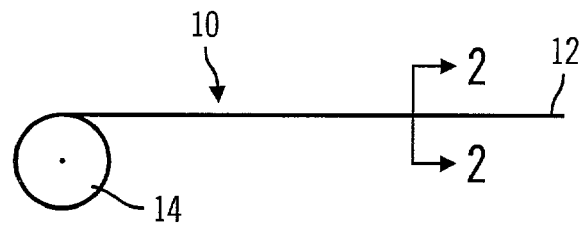

As shown in the drawings for purposes of illustration, the invention is embodied in an improved sensor and method of manufacturing the sensor. In preferred embodiments of the present invention, the sensor is a glucose sensor that utilizes glucose oxidase. However, alternative embodiments may use other materials, such as optical, fluorescence or electrical materials to sense the glucose levels, or may uses other materials to sense the presence of different analytes, such as, including but not limited to, HIV, viruses, medication levels, cholesterol, hormones, fluids or the like. Preferred embodiments are for use with humans. However, it will be recognized that further embodiments of the invention may be used in animals, laboratory tests, agriculture related testing, or the like.

According to embodiments of the inventive method, sensors are produced by deposition of a metal layer or layers followed by etching production methods. Subsequent layers are then added by electroplating. The metal layer(s) can be deposited on either a non-self supporting substrate, or in a preferred embodiment on a self-supporting substrate such as a polyimide tape. Thus, sensors can be produced cleanly and at high density on the substrate according to the inventive method; and in further embodiments, the sensors can be produced on one or both sides of the substrate.

Referring now to FIGS. 1–4, a substrate 10 is provided in accordance with a first embodiment of the inventive method. In preferred embodiments, substrate 10 is a flexible, self-supporting substrate in the form of a continuous tape 12 supplied from a reel 14. The continuous tape 12 is preferably formed from a polymeric material such as a polyimide. However, other flexible, self-supporting materials can be used. The thickness of tape 12 is preferably about $10\mu$ to $125\mu$. However, in alternative embodiments, thinner or thicker films from $5\mu$ to $500\mu$ may be used. In particular embodiments, sprocket holes 15 (see FIG. 2c) are formed in the substrate adjacent the outer edge of the tape 12 to facilitate manufacturing of the sensors through automated processes. For instance, the tape 12 is fed through stages that perform various steps of the methods described in this application. Sensor electrodes 20 can be formed on the tape 12 using techniques described in "3M Specifications and Design Guidelines, Microflex circuits for IC Interconnect Solutions," pages 1 –32 (the entire document), 1997 (3M Electronic Products Division, Austin Tex.), "3M Offers More Solutions for the Semiconductor Industry" the entire document, 1997 (3M Electronic Products Division, Austin Tex.), and "Microflex Solutions from 3M", the entire document, 1996 (3M Electronic Products Division, Austin Tex.), all of which are publicly available from 3M and are specifically incorporated herein by reference.

Alternatively, substrate 10 can be formed by a casting process, for example by spin-coating a layer of a liquid polyimide or other polymeric material onto a temporary glass carrier and then cured. Such substrates can be self-supporting or non-self supporting. The sensor electrodes 20 can be formed on the substrate 10 using techniques described in "Micron Wide Conductors and Spaces on . . . PZT, Alumina, Glass and Flexible Materials" 1 page, no date (Metrigraphics, Wilmington, Mass.), "Flexibel circuits at Extreme Density, 8 unnumbered pages of various dates (Metrigraphics, Wilmington, Mass.), and "Metrigraphics Ion Beam Etching Capability", 1 page, no date (Metrigraphics, Wilmington, Mass.), and all of which are publicly available and are specifically incorporated herein by reference.

Substrate 10 has an upper surface 16 and a lower surface 18. The substrate 10 is preferably cleaned, and subsequently at least one metal layer 20a is formed on the upper surface 16 of the substrate 10 by a deposition process (see FIG. 2a). A particularly preferred process is sputter deposition, or sputtering. Sputtering can be carried out using commercially available sputtering reactors using an RF (radio frequency). Magnetron sputtering can also be carried out; magnetron sputtering uses a magnetic field to concentrate electrons near the target surface to increase the deposition rate. Other known deposition processes, such as chemical vapor deposition (CVD) methods, can also be employed. The thickness of the deposited layer preferably ranges from about $0.05\mu$ to about $300.0\mu$, more preferably about $0.5\mu$ to about $25.0\mu$. When multiple layers are deposited, the total thickness of the layers preferably has a thickness within the foregoing ranges.

One or more metal layers can be deposited on the substrate 10 according to the inventive method. For example, two layers 20a and 20b of different metals can be deposited (see FIG. 2b). Exemplary metals include, but without limitation, elemental metals such as chromium, gold, copper, aluminum, nickel, tantalum and titanium, alloys such as Inconel and Nichrome, and mixtures thereof. The term "metal layer" is also intended to encompass layers that include one or more non-metallic elements in a mixture or chemical combination with one or more metallic elements, and thus also encompasses materials such as oxides, for example alumina. Reactive as well as non-reactive layers can be formed; reactive materials, such as tantalum oxide, chromium oxide, etc., are also intended to be encompassed by the term "metal layer." Specific combinations of metal layers that are useful according to the invention include chromium and copper; copper and gold; and chromium, gold and chromium; copper, nickel and gold; and chromium, copper, nickel and gold.

In particular embodiments, chromium forms the first sputtered metal layer. Chromium provides an additional benefit in promoting adhesion between certain polymeric materials, such as polyimides, and other metals. Other metal layers, such as nickel or the like, that promote adhesion can also be employed if desired.

Figure 2A:
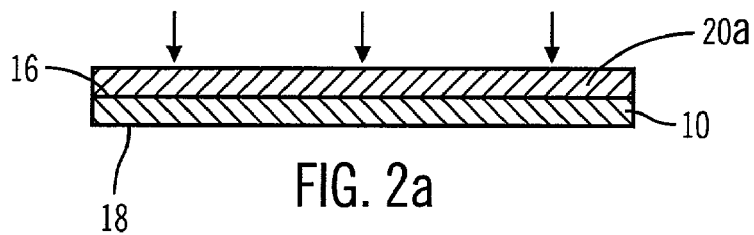
FIG. 2a is a cross-sectional view of the substrate as viewed along the line 2—2 in FIG. 1 with the inclusion of a sputter deposited layer.
Figure 2B:
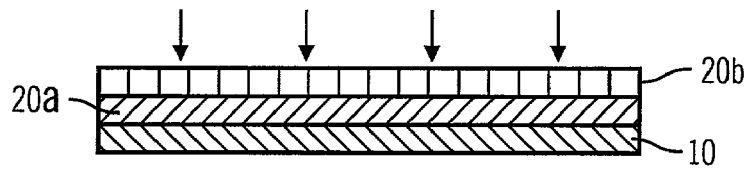
FIG. 2b is a cross-sectional view of the substrate with multiple sputter deposited layers.
Figure 2C:
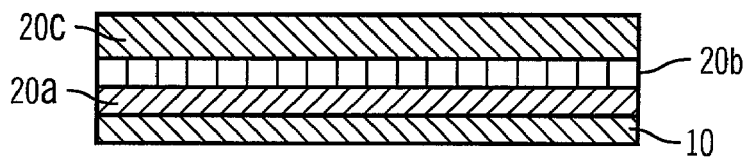
FIG. 2c is a cross-sectional view of the substrate with multiple sputter deposited and plated layers.
Figure 2D:
FIG. 2d is a cross-sectional view of the sensor electrode after it has been etched back and the substrate after it has been formed with sprocket holes.

As shown in FIG. 2d, in particular embodiments, subsequent to the sputter deposition step but prior to an etching step, one or more metal layers 20c can be plated on the upper surface of the sputter deposited metal layer (or the uppermost sputter deposited layer if more than one such layer is prepared). Such layers, in preferred embodiments, are comprised of copper. However, in alternative embodiments, other metals, such as nickel, chromium, gold, or the like, may be plated onto the layers used to form the sensor electrodes.

After the sputter deposition of the metal layer(s), and/or one or more layers are applied by plating, an etching process is carried out in order to form the sensor electrode 20 (see FIG. 2d). Any conventional etching process can be employed. For example, the etching processes described above and in U.S. Pat. No. 5,391,250 issued Feb. 21, 1995 to Cheney, II et al. and entitled "Method of Fabricating Thin Film Sensors", which is incorporated herein in its entirety by reference, may be used to form one or more sensor electrodes. In alternative embodiments, the one or more metal layers applied by plating prior to etching may be omitted and just the sputtered layers are etched. Preferred embodiments form the sprocket holes 15 by etching at the same time that metal etching process is carried out. Alternative embodiments may form the sprocket holes 15 before or after the etching of the metal layer(s). Sprocket holes 15 may be formed by other methods, such as water knife, laser ablation, punching, cutting, or the like.

Figure 2E:
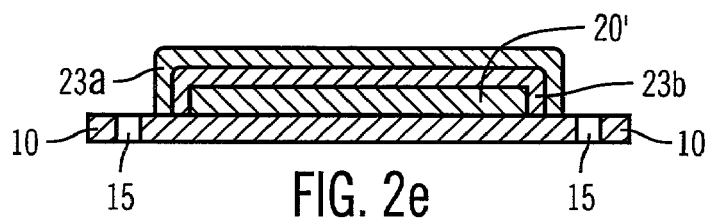
FIG. 2e is a cross-sectional view of a sensor electrode after additional layers have been plated onto the sensor electrode.

In further embodiments, subsequent to the etching step one or more additional metal layers 23a, 23b can be plated on the sensor electrode(s) 20' (see FIG. 2e). The optional additional plating step is advantageous in providing a protective coating over the sputter-deposited metal layers, including the sides thereof. In particular embodiments, layers of copper; copper and gold; or copper, nickel and gold are plated after the etching step. In preferred embodiments, gold is plated over the sensor electrodes 20' as the final layer 23b to seal in all of the other layers.

Figure 3A:
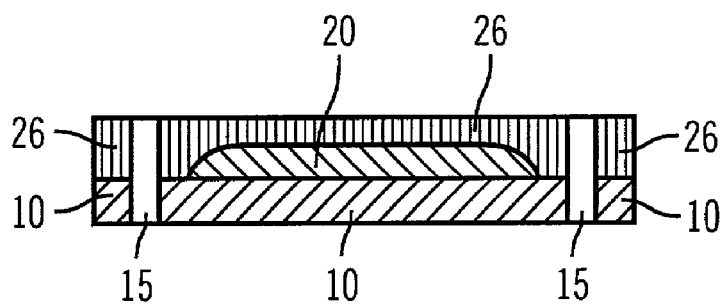
FIG. 3a is a cross-sectional view of the substrate and sensor electrode after being covered by a polymer coating.
Figure 3B:
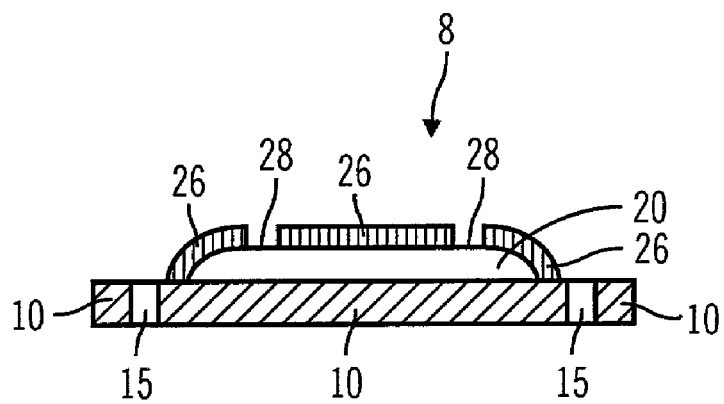
FIG. 3b is a cross-sectional view of the substrate and sensor electrode after the polymer coating has been etched back.

As shown in FIG. 3a, in a preferred embodiment, prior to separation from the remainder of the substrate, the sensor can be provided with a polymeric coating 26, preferably formed from a non-toxic, biocompatible polymer. For instance, the polymer coating 26 provides an insulative and/or protective coating that covers the substrate 10 and the sensor electrodes 20. Exemplary useful polymers include, without limitation, polyimide, biocompatible soldermasks, epoxy acrylate copolymers, or the like. In preferred embodiments, the polymers are photo-imaginable to permit portions of the polymers to be removed for exposure of contacts, electrodes for application of sensor chemistry, or the like. Portions of the coating polymer are masked to form a pattern, which is them exposed and developed to remove the portions of the polymer coating 26 for further processing of the sensor 8. In alternative embodiments, the coating polymer may be removed by other methods, such as by laser ablation, chemical milling, or the like. Use of a secondary photo resist can be employed to target specific sites for removal. As shown in FIG. 3b, the coating polymer 26 is etched (ablated, milled, or the like) back to expose windows (or openings) 28 to expose the contact pads to permit connection with a monitoring device (discussed below) and to form windows (or openings) 28 over the sensor electrodes 20 to allow sensor chemistry materials to be applied to the exposed sensor electrodes 20 to complete the manufacture of the sensors 8.

In further embodiments, the exposed areas that form windows (or openings 28) are plated with additional layers of metal. This saves money and can reduce the thickness of the sensor electrodes, except where the thickness or layer is required. Plating after forming the windows (or openings) 28 also allows the plating to fill in any potential leaks around the windows (or openings) 28 caused by gaps between the polymer layer and the sensor electrodes. Additionally, if the final metal layer is plated after the last etching and coating step, the surface of the final metal layer is in its best condition for application of enzymes and membranes. Thus, doing a final plating step increase reliability and predictability of sensor performance. In preferred embodiments, the final metal layer is gold. However, in alternative embodiments, other final metal layers, such as platinum, iridium, chromium, copper or the like may be used.

Figure 4:
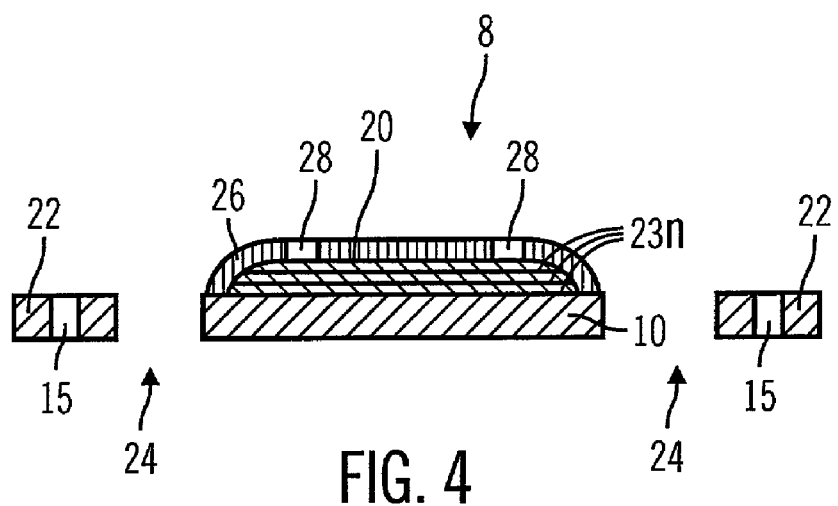

After completion of the etching and optional plating steps and any polymer coating steps, the sensor 8, including a portion of the substrate underlying the metal layer(s) 23n forming the sensor electrode 20 and any polymer coating 26, is removed from the remainder of the substrate (see FIG. 4). In a preferred embodiment, the sensor is removed from the remainder portions 22 of the substrate 10 by cutting along lines 24, for example using a laser. Other known cutting devices, such as blades, ultrasonic, water knifes, or the like, can also be used.

Sensors formed according to the inventive method are usefully employed in a variety of known sensor sets. Exemplary sensor sets are illustrated in FIGS. 5–11, generally similar to those described herein, not including a bead, into a sensor set generally similar to that described in U.S. Pat. No. 5,586,533, to Halili et al., and entitled "Transcutaneous Sensor Insertion Set", and U.S. Pat. No. 5,954,643 issued Sep. 21, 1999 to Van Antwerp et al. and entitled "Insertion Set for a Transcutaneous Sensor", which are incorporated herein in its entirety by reference. In an embodiment illustrated in FIGS. 5–10, a sensor set referred to generally by the reference numeral 110 is provided for transcutaneous placement of a flexible sensor 112 (see FIG. 6) at a selected site within the body of a patient. The insertion set 110 includes a rigid hollow slotted insertion needle 114 for quick and easy placement at a desired placement site (e.g., transcutaneous, intraperitoneal, peritoneal, etc.) of a cannula 115 with a distal segment 116 of the sensor 112 therein. The distal segment 116 has at least one sensor electrode 118 (three are illustrated, which generally correspond to the sensor electrode 20 described above), formed by deposition as described above, exposed to patient fluid through a window 119 in the cannula 115. The insertion needle 114 is then withdrawable to leave the cannula 115 with the sensor distal segment 116 and the sensor electrodes 118 in place at the selected site.

The sensor set 110 is particularly designed for facilitating accurate placement of a flexible thin film electrochemical sensor of the type used for monitoring specific blood parameters representative of patient condition. The sensor set 110 is designed to place the sensor at a selected site within the body of a patient, in a manner minimizing patient discomfort and trauma. In one preferred application, the sensor 112 may be designed to monitor blood glucose levels, and may be used in conjunction with automated or semiautomated medication infusion pumps of the external or implantable type as described in U.S. Pat. Nos. 4,562,751; 4,678,408; 4,685,903 or 4,573,994, to deliver insulin to a diabetic patient.

The flexible electrochemical sensor 112 is constructed according to the methods described herein. The sensor electrodes 118 (shown in exaggerated form in the drawings) are exposed for direct contact with patient interstitial fluid, or the like, when the sensor is transcutaneously placed. The distal segment 116 is joined to a proximal segment 120, (see FIG. 6) the end of which terminates in suitable conductive contact pads or the like. As is known in the art, and illustrated schematically in FIG. 6, the proximal segment 120 and the contact pads are adapted for electrical connection to a suitable monitor 122 for monitoring patient condition in response to signals derived from the sensor electrodes 118 in manners known to those skilled in the art.

Figure 5:
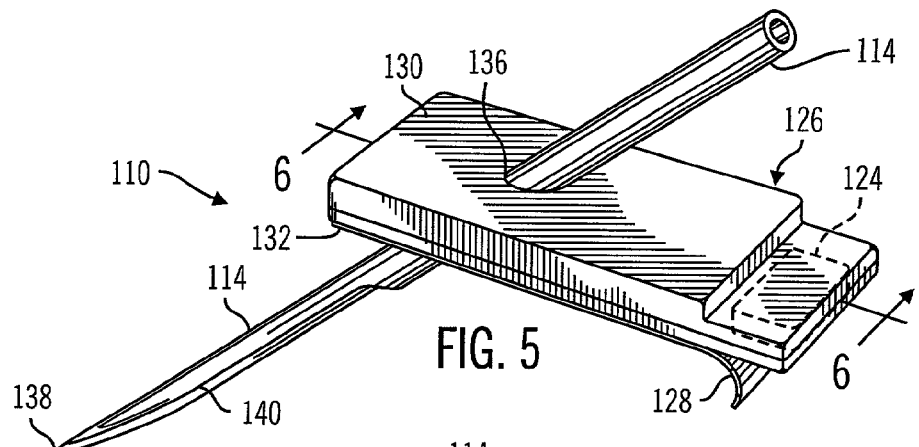
FIG. 5 is a perspective view illustrating a sensor set that includes a sensor formed according to the invention.
Figure 6:
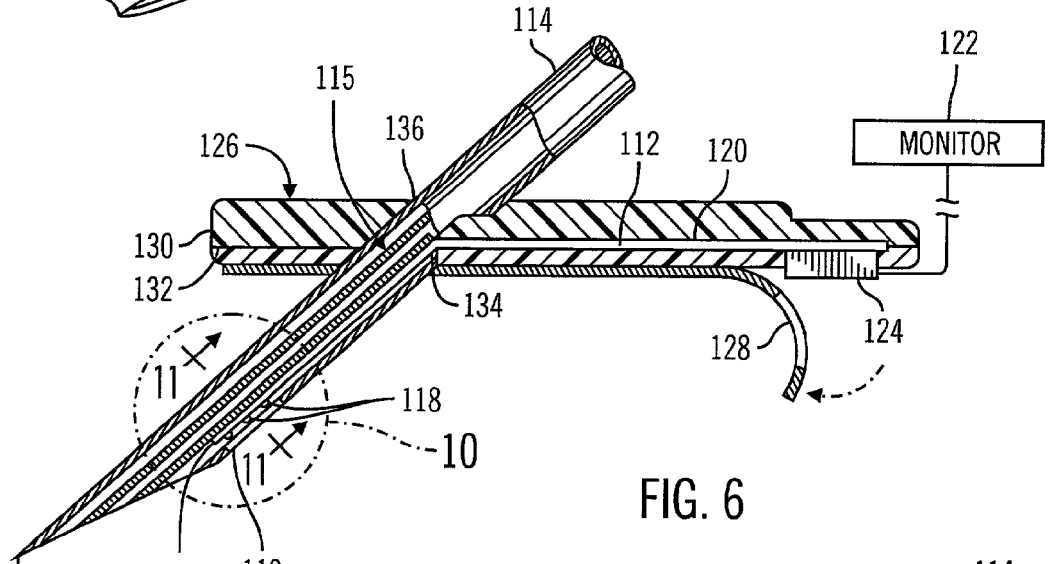
FIG. 6 is an enlarged longitudinal vertical section taken generally on the line 6—6 of FIG. 5.
Figure 7:
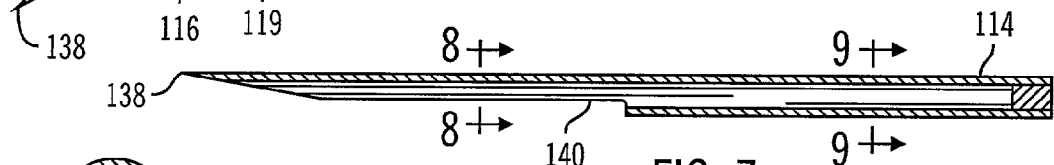
FIG. 7 is an enlarged longitudinal sectional of a slotted insertion needle used in the insertion set of FIGS. 5 and 6.
Figure 8:
FIG. 8 is an enlarged transverse section taken generally on the line 8—8 of FIG. 7.
Figure 9:
FIG. 9 is an enlarged transverse section taken generally on the line 9—9 of FIG. 7.

According to the embodiment of FIGS. 5 and 6, the sensor 112 is carried by a mounting base 126 adapted for placement onto the skin of a patient. An exemplary mounting base 126 comprises an enlarged and generally rectangular pad having an underside surface coated with a suitable pressure sensitive adhesive layer, with a peel-off paper strip 128 normally provided to cover and protect the adhesive layer, until the insertion set 110 is ready for use. As shown in FIGS. 5 and 6, the mounting base comprises upper and lower layers 130 and 132, with the proximal segment 120 of the sensor 112 sandwiched between the layers 130 and 132. The proximal sensor segment 120 has a forwardmost end joined to the distal segment 116 which is folded angularly to extend downwardly through a slot 134 formed in the lower base layer 132.

The insertion needle 114 is adapted for slide-fit reception through a needle port 136 formed in the upper base layer 130 and further through the lower slot 134 in the lower base layer 132. As shown, the insertion needle 114 has a sharpened tip 138 and an open slot 140 which extends longitudinally from the tip 138 at the underside of the needle to a position at least within the slot 134 in the lower base layer 132. Above the mounting base 126, the insertion needle 114 can have a full round cross sectional shape and is desirably closed at a rear end. In a more specific preferred embodiment, the slotted needle 114 has a part-circular cross sectional shape, with an arcuate dimension or span greater than 180°, such as an arcuate dimension of about 210°. This leaves a longitudinal slot in the needle with an arcuate dimension of about 150°.

Figure 10:
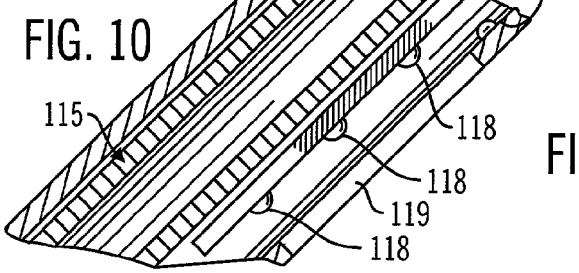
FIG. 10 is an enlarged fragmented sectional view corresponding generally with the encircled region 10 of FIG. 6.
Figure 11:
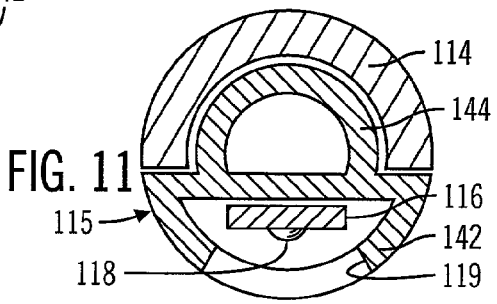
FIG. 11 is an enlarged transverse section taken generally on the line 11—11 of FIG. 6.

The cannula 115 illustrated in FIGS. 10 and 11 comprises a first portion 144 of part circular cross section fitted within the insertion needle 114 to extend downwardly from the mounting base 126. This cannula 115 is preferably constructed from a suitable medical grade plastic or elastomer, such as polytetrafluoroethylene, silicone, etc., to define an open lumen 142 in a second portion for receiving, protecting and guidably supporting the distal segment 116 of the sensor 112. The cannula 115 has one end fitted into the slot 134 formed in the lower layer 132 of the mounting base 126, wherein the cannula 115 is desirably secured to the mounting base by a suitable adhesive or other selected attachment methods. From the mounting base 126, the cannula extends angularly downwardly with the first portion 144 nested within the insertion needle 114, terminating slightly before the needle tip 138. Importantly, at least one window 119 is formed in the lumen 142 near the distal end, in general alignment with the sensor electrodes 118, to permit direct electrode exposure to patient body fluid when the sensor is transcutaneously placed.

According to the preferred embodiment illustrated FIG. 11, the second portion 142 of the cannula 115 has a part-circular cross sectional shape which cooperates with the part-circular shape of the insertion needle 114 to define a substantially full-circle geometry for facilitated insertion through the patient's skin. The first portion 144 of the cannula 115 has a smaller cross sectional profile than the second portion 142, for sliding nested reception into the needle 114. The needle 114 and first cannula portion 144 are thus mechanically interlocked to prevent lateral dislocation of the cannula 115 from the insertion needle, while permitting longitudinal sliding motion of the needle over the cannula first portion 144. The distal or free end of the cannula second portion 142 is appropriately cut or otherwise set at an oblique angle, as viewed in FIG. 6, to form a continuation of the angle-cut tip 138 of the insertion needle.

In use, the sensor set 110 permits quick and easy placement of the sensor distal segment 116 at a selected site within the body of the patient. More specifically, the peel-off strip 128 (FIG. 5) is removed from the mounting base 126, at which time the mounting base 126 can be pressed onto and seated upon the patient's skin. The set may be inserted by hand or inserted with an insertion tool, such as disclosed in U.S. patent application Ser. No. 09/215,356 (PCT No. US98/26978) filed Dec. 18, 1998, and entitled "Insertion Device for an Insertion Set and Method of Using the Same", which is incorporated herein by reference. During this step, the insertion needle 114 pierces the patient's skin and carries the protective cannula 115 with the sensor distal segment 116 therein to the appropriate transcutaneous placement site. During insertion, the cannula 115 provides a stable support and guide structure to carry the sensor to the desired insertion site.

When the sensor 112 is placed at the insertion site, with the mounting base 126 seated upon the patient's skin, the insertion needle 114 can be slidably withdrawn from the patient. During this withdrawal step, the insertion needle 114 slides over the first portion 144 of the protective cannula 115, leaving the sensor distal segment 116 with electrodes 118 at the selected insertion site. These electrodes 118 are directly exposed to patient body fluid via the window 119. The sensor proximal segment 120 is appropriately coupled to the monitor 132, so that the sensor 112 can then be used over a prolonged period of time for taking chemistry readings, such as blood glucose readings in a diabetic patient. If desired, the first portion 144 of the cannula 115 can be hollow as shown to form a second lumen available to deliver medication and/or sensor calibration fluid to the vicinity of the electrodes 118, or alternately to withdraw patient fluid such as blood for analysis.

Sensors produced as described above can also beneficially be included in sensor sets such as those described in PCT Application Serial No. WO 98/56293, to applicant MiniMed Inc., published Dec. 17, 1998, which corresponds to copending, commonly assigned U.S. patent application Ser. No. 08/871,831, filed Jun. 9, 1997, entitled "Insertion Set for a Transcutaneous Sensor", now U.S. Pat. No. 5,954,643, and in copending, commonly assigned U.S. patent application Ser. No. 09/161,128, to Mastrototaro et al., filed Sep. 25, 1998, now U.S. Pat. No. 5,951,521, the disclosures of each of which are incorporated in their entireties herein by reference.

Figure 12A:
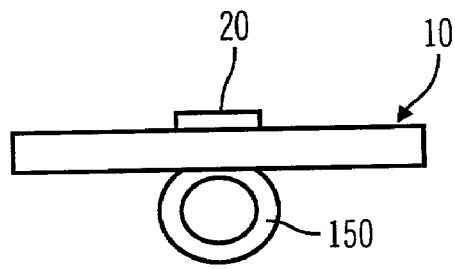
FIGS. 12a–b are transverse sections of alternative embodiments of a sensor produced according to the invention that include tubular (FIG. 12a) or solid (FIG. 12b) beads.
Figure 12B:
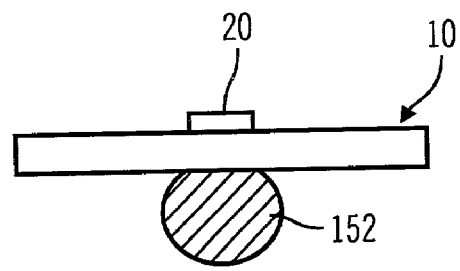
Figure 13:
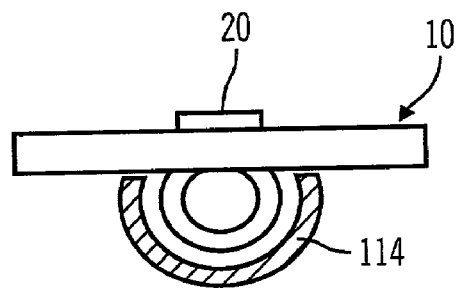
FIG. 13 is a transverse section illustrating the engagement of the sensor of FIG. 12a and a slotted insertion needle.
Figure 14:
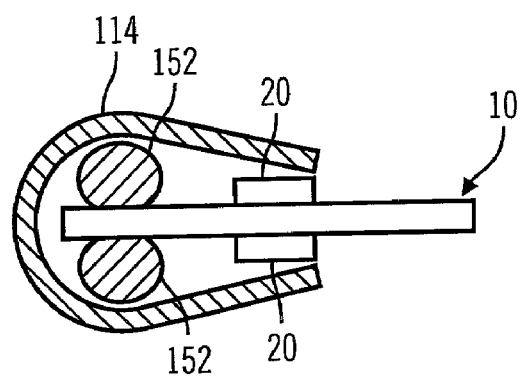
FIG. 14 is a transverse section illustrating another alternative embodiment of a sensor of the invention including beads on each side of the sensor, and the engagement of the sensor with a slotted insertion needle.
Figure 15A:
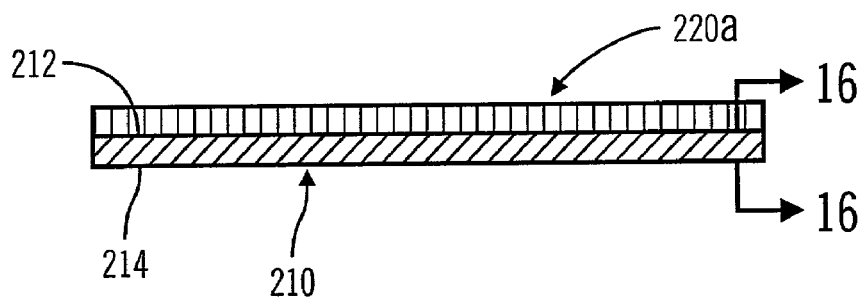
FIGS. 15a–b are side sectional views illustrating deposition of a metal layer (FIG. 15a) or metal layers (FIG. 15b) on a flexible substrate.
Figure 15B:
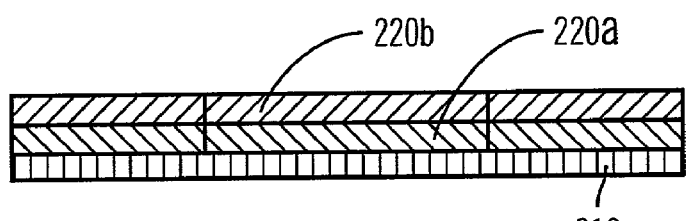

In an alternative method according to the invention, illustrated in FIGS. 12–14, one or more beads are provided to the sensor. The beads facilitate engagement of the sensors directly with a slotted insertion needle without the need for a cannula. Use of beads on each side of the substrate that is used to form the sensor, can also enable production of sensors having sensor electrodes on each side of the substrate.

As shown in FIGS. 12a–b, a bead, which can be hollow (see FIG. 12a, bead (or tube) 150) or solid (FIG. 12b, bead 152), is formed on the lower surface 18 of the substrate 10. The bead can be formed on the surface of the substrate by a variety of means, such as by securing a cylindrical element to the surface, by molding, laminating, or the like. The bead can be provided either before or after the sensor is removed from the remainder of the substrate 10. Once formed, the bead directly engages a slotted insertion needle 114 (FIG. 13) of a sensor set as described herein.

In FIG. 14, an alternative embodiment of a sensor includes beads, preferably solid beads 152, formed on both the upper surface 16 and the lower surface 18 of the substrate 10. This embodiment is useful in preparing sensors having sensor electrodes 20 on each side of the substrate. Such two-sided sensors can be used, for example, to detect two different body conditions, such as blood glucose level and the presence of an antibody, simultaneously, when appropriate electrode chemistries are provided; or the same body condition, such as glucose levels, by providing a cross-check using two different sensor readings.

Another alternative method according to the invention is illustrated in FIGS. 15–21. In FIG. 15a, at least one metal layer 220a is deposited on the upper surface 212 of the substrate 210 and formed into a sensor electrode as described above. Two or more metal layers can be deposited to form the sensor electrode, as illustrated in FIG. 15b, in which first and second metal layers 220a, 220b are sequentially deposited on upper surface 212 of substrate 210. Also, although formation of one sensor electrode is illustrated for the sake of clarity, two or more sensor electrodes 220 can be formed on the same substrate by deposition of appropriate metal layers at different sites on the substrate. And multiple sensors may be formed on the substrate at the same time. The method of forming the sensor electrode 220 may be carried out as described for the sensor electrode 20 above and as shown in FIGS. 1–4.

Figure 16:
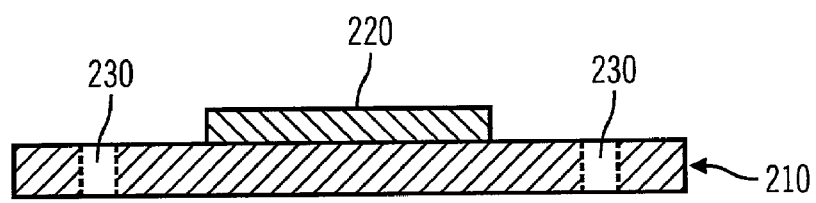

After formation of the sensor electrodes 220 on the upper surface 212 of substrate 210, substrate 210 is perforated on either side of the metal layer(s) (see FIG. 16). Perforations 230 can be formed by any desired means, for example by laser cutting, etching, the use of a blade or other appropriate tool, or the like. The perforations preferably are sized to permit flow of a fluid, in particular a liquid polymer, through the perforations. In alternative embodiments, the perforations may be formed at the same time the sprocket holes on the tape 12 (as described above) are formed. Preferred embodiments use chemical etching to form the perforations.

Once the perforations 230 are formed, the lower surface 214 of substrate 210 is secured to a mold 232. The mold 232 may be attached while the substrate 210 is still a part of the tape 12, or after the substrate 210 has been cut from the tape 12. In addition, cut sections of the tape 12 may include one or more sensors. The mold may also be applied to substrates formed as sheets rather than tapes 12, as described above.

Figure 17:
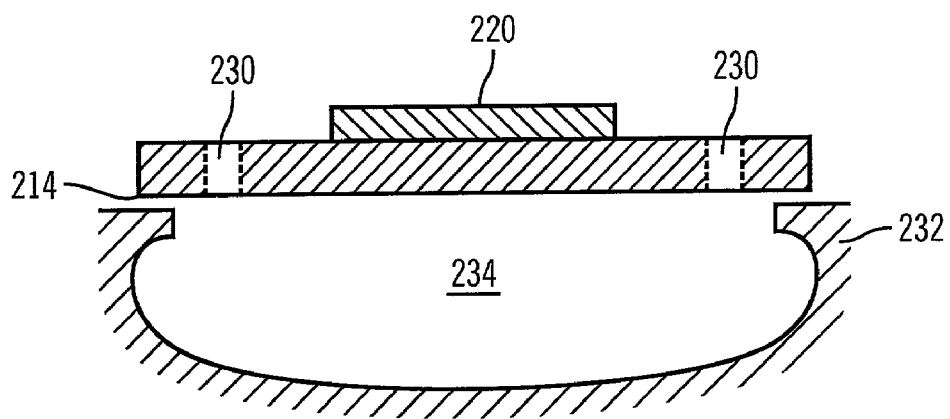
Figure 18A:
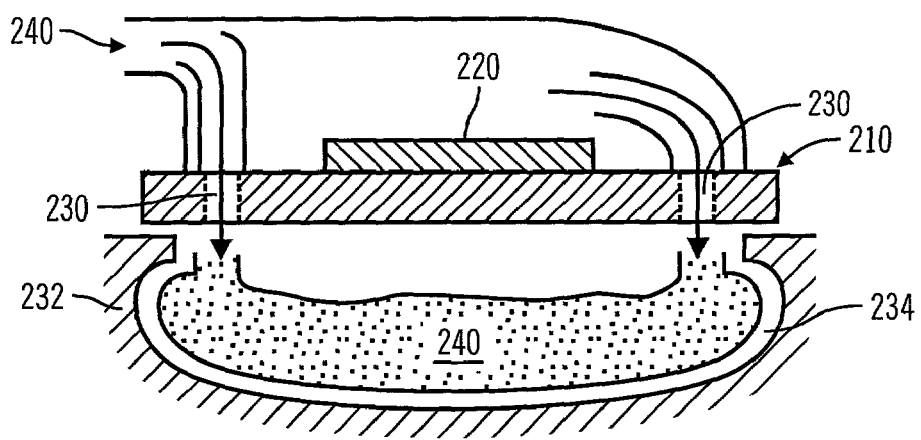
FIGS. 18a–b illustrate provision of a liquid polymer through the perforations formed in the substrate into the mold channel (FIG. 18a) and its beading over the upper surface of the substrate and the metal layer (FIG. 18b)
Figure 18B:
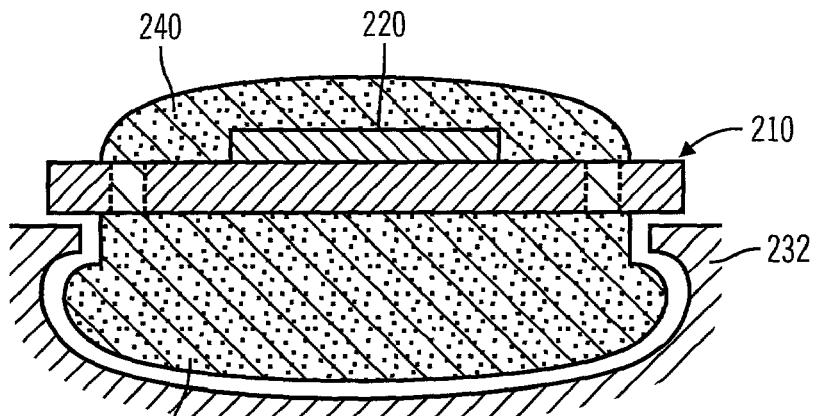
Figure 19:
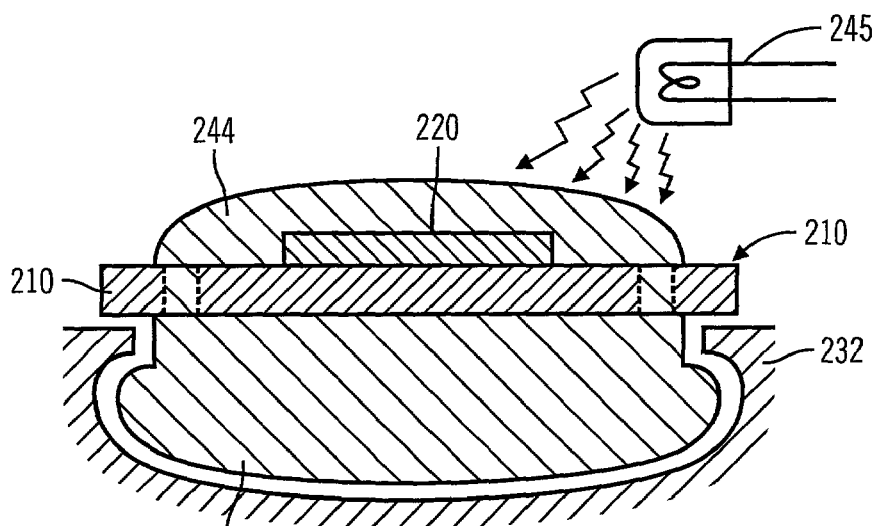

Mold 232, as shown in FIG. 17, has defined in its upper surface adjacent to the lower surface 214 of substrate 210 a channel 234, which preferably extends below the metal layer(s). Next, a liquid polymer 240 is flowed through the perforations 230 and into the channel 234 in mold 232. The liquid polymer is preferably a biocompatible polymer, such as polyurethane, polycarbonate, silicone, acrylic or other thermoplastics. In preferred embodiments, the polymer flow is continued until the liquid polymer fills the mold and overflow to form a bead on the upper surface 212 of substrate 210 and the upper surface of the metal layer(s). This upper bead can also provide an upper protective coating to the sensor. See FIGS. 18a–b.

The liquid polymer 240 is then cured, for example by exposure to a source 245 of actinic radiation, heat or the like (see FIG. 19) to form bead 242 on the lower surface 214 of substrate 210 and coating 244 on the upper surface 212 and over the metal layer(s). After completion of the curing step, mold 232 is removed from contact with the substrate 210, for example by sliding the mold laterally away from the substrate in the direction defined by channel 234 (see FIG. 20). Finally, the finished sensor, including the metal layer(s), the cured polymer and the portion of the substrate therebetween and between the first and second perforations, is removed from the remainder of the substrate by separating the substrate adjacent the perforations. As shown in FIG. 21, the sensor 260 is separated from the remainder 262 of the substrate along separation lines 254, 256, which are formed, for example, by cutting using a laser, etching, a blade or another appropriate tool, or the like.

The liquid polymer 240 can be flowed over the entire surface of the metal layer(s) if desired. Preferably, however, one or more portions of the metal layers remain exposed. In this preferred alternative, the perforations 230 are formed such that they include one or more perforation gaps, that is, segments that include no perforations. The surface of the metal layer(s) extending between these perforation gaps remains uncovered by the liquid polymer, which does not bead over such areas.

Figure 20:
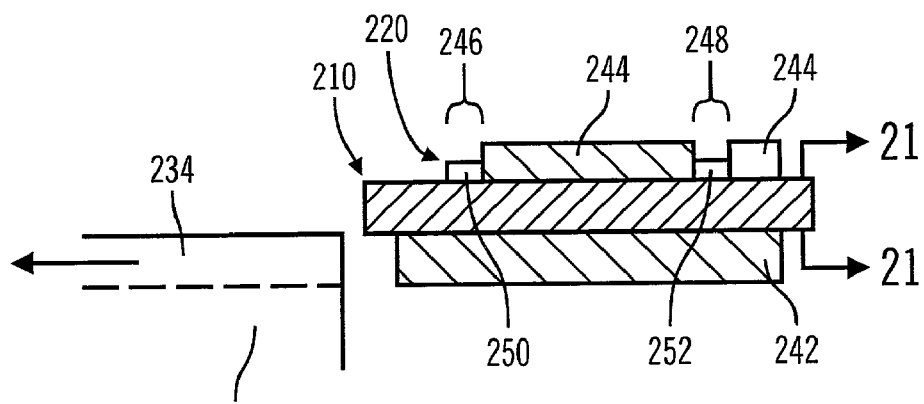
Figure 21:
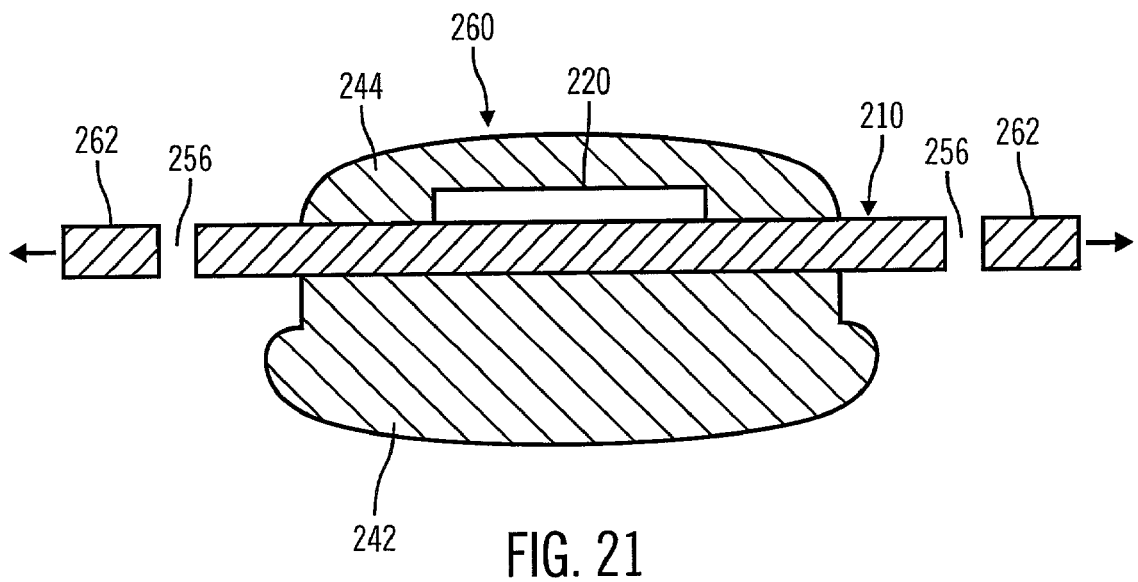

As shown in FIG. 20, perforation gaps 246, 248 adjoining the perforations 230 allow proximal segment 250 and distal segment 252 of the sensor electrodes 220 to remain exposed without the liquid polymer 240 beading up over these segments. Proximal segment 250 can, as discussed above, terminate in a conductive contact pad, while the distal segment 252 can include a portion that is provided with an appropriate electrode chemistry.

Figure 22:
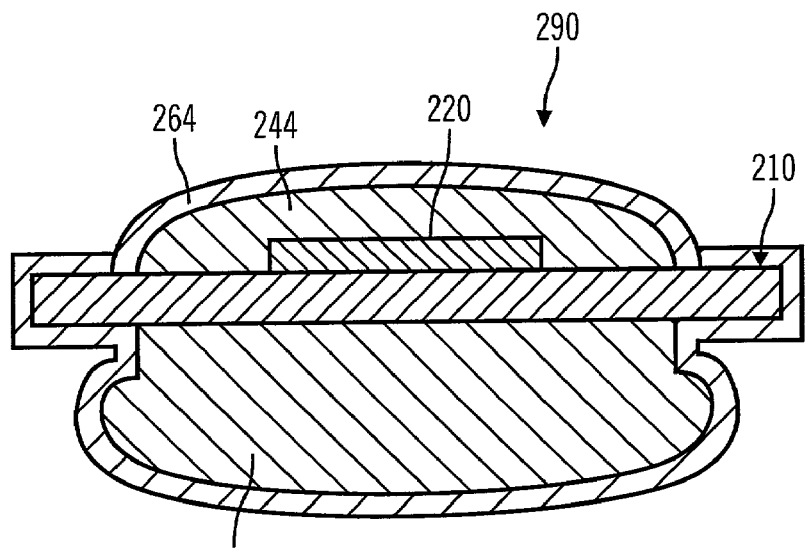
FIG. 22 is a sectional view of an alternative embodiment of the inventive method in which a sensor membrane is provided after the liquid polymer is supplied.

In an alternative embodiment, additional protective layers or membranes can be provided to the upper surface of the substrate and the metal layer(s). In FIG. 22, a sensor membrane 264 is placed above the metal layer and adhered to the liquid polymer prior to, or after, curing to improve biocompatibility of the sensor.

Sensors including beads can also be prepared by methods other than those set forth above. For example, sensors can be prepared by any of the methods set forth in U.S. patent application Ser. No. 09/034,433, to Say et al., corresponding to PCT Application No. PCT/US99/03781, published Sep. 10, 1999 under International Publication No. WO 99/45375 and incorporated herein in its entirety by reference, and provided with beads according to the methods set forth herein.

Figure 23A:
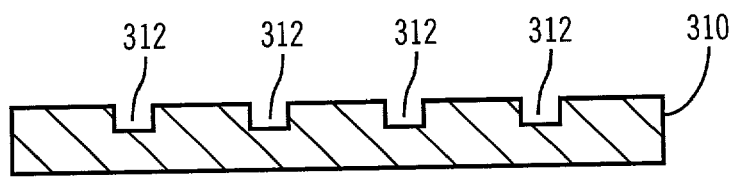
FIGS. 23a–b illustrate a first alternative method in which channels are formed in a substrate and subsequently filled with a conductive material to form the sensor electrodes, FIG. 24 illustrate a second alternative method in which sensor electrodes are formed electrographically using a conductive toner.

In one such method, one or more channels 312 are formed in the substrate 310, for example by an embossing process using an embossing die or roller (see FIG. 23a). Other methods for forming the channels, such as the use of a laser, or photolithography and etching of the substrate can also be employed if desired.

Figure 23B:
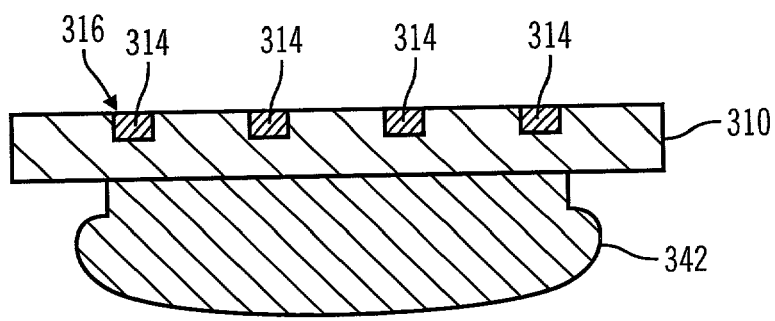

Once the channels 312 have been formed, a conductive material 314 is placed, flowed, applied, filled, flooded or otherwise disposed within the channels 312 to form the sensor electrodes 316 (FIG. 23b). The conductive material can be applied as a precursor conductive material having a liquid form. An exemplary precursor conductive material is a carbon-based ink that can be flooded in liquid form into the channels 312. Other conductive inks or pastes that include carbon or metal, such as gold, copper or silver, can also be used. Other techniques for applying the conductive material or precursor conductive material, including spraying, coating, flooding, applying with a saturated roller, pumping, as well as impact and non-impact printing methods such as electrostatic or magnetographic methods.

Figure 24:
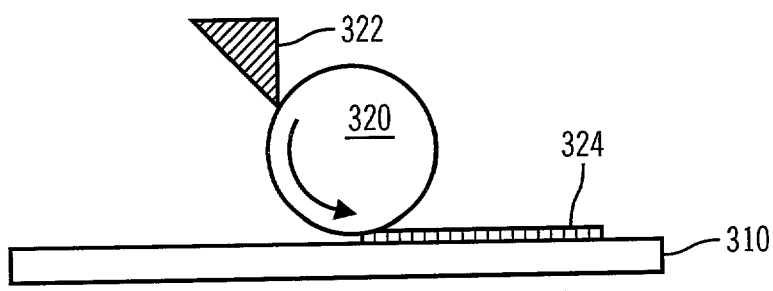

According to a second embodiment, a non-impact process is used to form the sensor electrodes 324. Exemplary non-impact processes include electrophotography and magnetography, in which an image of the conductive traces is electrically or magnetically formed on a drum 320. The image attracts a toner material 322 to the drum. The toner 322 material is subsequently transferred to the substrate 310, for example by rolling, followed preferably by a curing step to adhere the toner material to the substrate. See FIG. 24. Other useful non-impact processes include ink jet printing and piezo jet printing, in which an image is formed by ejection of a conductive material, such as a conductive ink, onto the substrate. Still other useful non-impact processes include the use of photosensitive resins to form a layer on the substrate in which channels are defined, followed by filling the channels with conductive material to form the sensor electrodes.

Figure 25A:
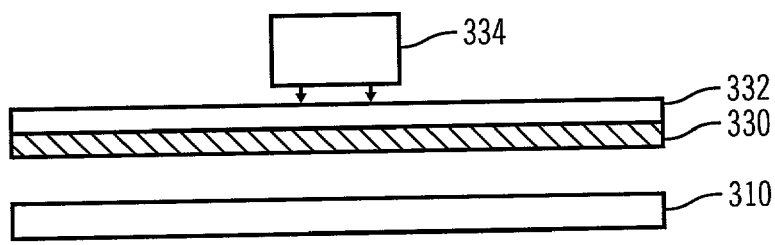
FIGS. 25a–b illustrate a third alternative method in which sensors are formed by a printing process.
Figure 25B:
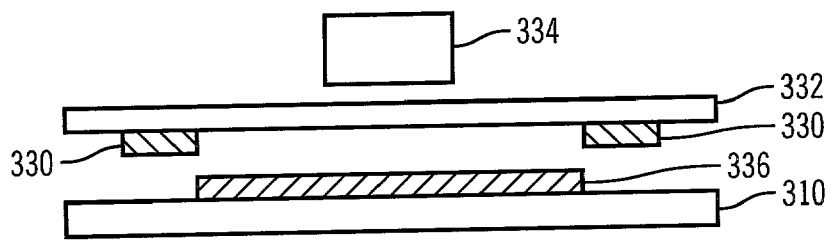
Figure 26:
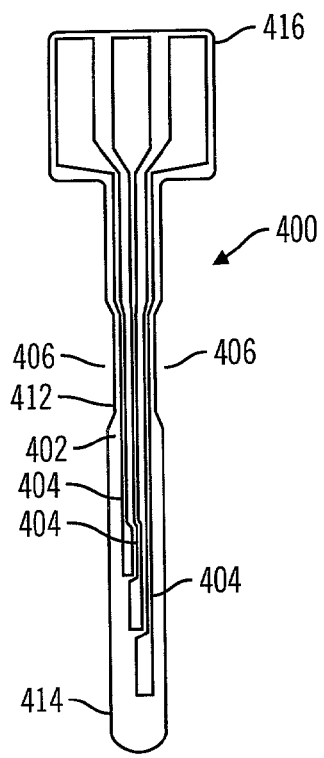
FIG. 26 is a top plan view of a sensor in accordance with another embodiment of the present invention.
Figure 27:
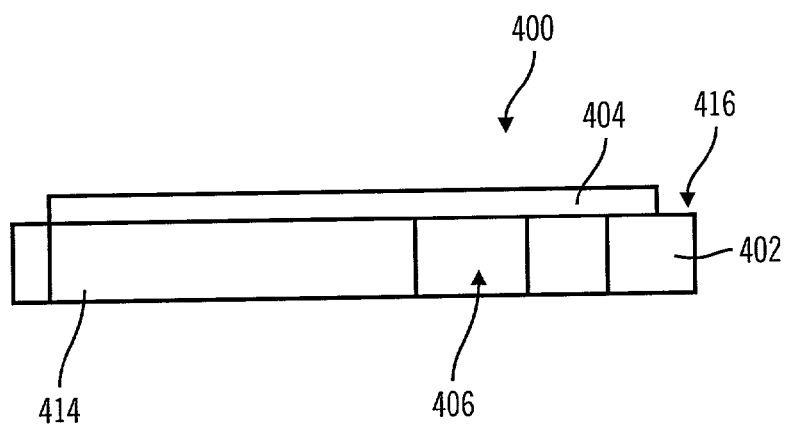
FIG. 27 is a side plan view of the sensor shown in FIG. 26.
Figure 28:
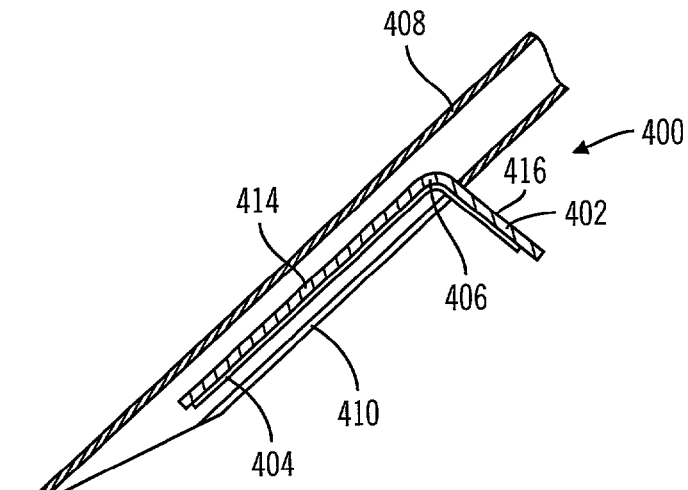
FIG. 28 is a partial cross-sectional view of the sensor of FIG. 26 inside of an insertion needle.
Figure 29:
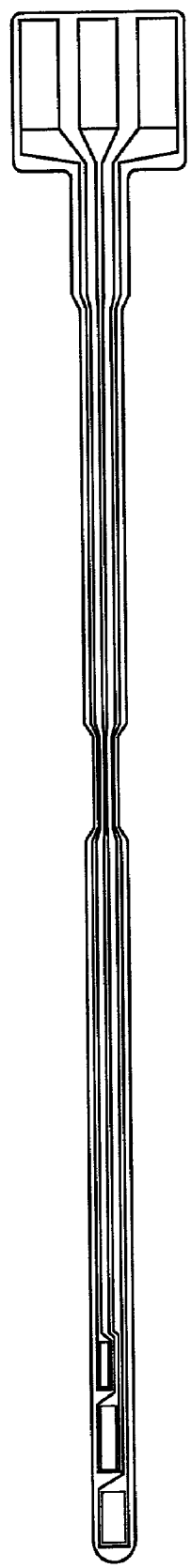
FIG. 29 is a top plan view of another sensor similar to the embodiment of the sensor shown in FIG. 26.

According to a third embodiment, a film of conductive material 332 is formed, for example, as a continuous sheet or as a coating layer deposited on a carrier film 330. The film is brought, for example, between a print head 334 and the substrate 310. A pattern of sensor electrodes 336 is formed on the substrate 310 using the print head. The conductive material is transferred by pressure and/or heat to the substrate 310. See FIGS. 25a–b. Channels can be formed in the substrate as a result of the printing process, or alternatively the conductive material can be deposited on the substrate substantially without the formation of depressions or channels.

Once the sensor electrodes have been formed, a bead 342 can be provided in accordance with the methods described above.

FIGS. 26–29 illustrate a sensor 400 formed in accordance with another embodiment of the present invention. The sensor 400 includes a substrate 402 and at least one sensor electrode 404 formed from one or more conductive layers. In particular embodiments, the layers are formed from metal. However, alternative embodiments may utilize semiconductors, conductive polymers, DNA, RNA, molecular wires, or the like. The substrate 402 and the sensor 404 are formed and process by methods similar to those described above in the other embodiments. However, in this embodiment, the substrate 402 is formed from a thicker film (from a reel or as a sheet) so that no bead is required. The thickness of the substrate ranges from approximately $25\mu$ to $350\mu$. In further embodiments, thicker films may be used up to $750\mu$ or thinner films down to $5\mu$ may be used, with the thickness being determined by the strength of the substrate 402 material, the substrate material's resistance to tearing, the flexibility of the substrate material, or the like. For instance, if the substrate is contained within a slotted needle (or supporting structure) during insertion, a comparable normal or thinner thickness to the other embodiments described above may be used.

The sensor 400 is formed to obviate the need for a sensor set housing that remains attached to the body or the use of an additional bead, as described above in FIGS. 5–25b. To achieve this capability, the substrate 402 is formed (or cut) to include one or more notches 406. The notches 406 create a necked down region in the sensor 400 that allows the sensor 400 to slide into a slotted needle 408 that has a slot 410 that is narrow enough to permit passage of the necked down region 412 of the sensor 400, but prevent the non-necked down region 414 of the sensor 400 from pulling out of the slotted needle 408 through the slot 410. The slot 410 does permit the necked down region 412 of the sensor 400 to slide down the slot 410.

To insert the sensor, a sensor 400 is placed inside a slotted needle 408 by sliding the necked down region 412 into the slot 410 of the slotted needle 408 so that the non-necked down region 414 is slid up and into the interior of the slotted needle 408, while a connection region 416 remains outside of the slotted needle. The slotted needle 408, including the sensor 400, is inserted into a body (not shown). The sensor 400 is held against the body by the connection region 416 and the slotted needle 408 is then pulled out of the body (alternatively, the sensor may be included in a sensor set that holds the needle and the sensor). As the slotted needle 408 is pulled from the body, the necked down region 412 slides down the slot 410 of the slotted needle 410 and remains implanted in the body. Thus, in this embodiment, a sensor set and bead are not required, and the substrate 402 is of sufficient strength to remain in the body without any other support structures. In particular embodiments, the sensor may fit within a 21 gauge to a 27 gauge slotted needle for easy insertion into the skin.

In an alternative of these embodiments, to provide for the manufacture of a narrower sensor in width, with the aim to further minimize the size of the needle used to surround the sensor during insertion, several different approaches to sensor electrode layouts may be used. In one embodiment, two electrodes 502 and 504 are formed on one side 506 of the sensor 500 and a single electrode 508 is formed on the other side 510 (see FIGS. 30(a) and 30(b)). This allows the size of the electrodes to be maintained with a consummate reduction in width. In further alternative embodiments, one electrode 552 is formed on one side 554 of the sensor 550 and another single electrode 556 is formed on the back 558 of the sensor 550 (see FIGS. 31(a) and 31(b)). A third electrode 560, if needed, such as a ground (or reference) electrode is formed before the necked down region of the sensor to form an electrode that rests on (or is in contact with) the top of the skin (see FIG. 31 (a). This substantially reduces the width of the sensor permitting small gauge needles to be used. For instance slotted needles of 22 gauge to 28 gauge may be used.

While the description above refers to particular embodiments of the present invention, it will be understood that many modifications may be made without departing from the spirit thereof. In particular, it is to be understood that the exemplary embodiments set forth herein, whether referred to as preferred embodiments or otherwise, are in no way to be taken as limiting the scope of the present invention. The accompanying claims are intended to cover such modifications as would fall within the true scope and spirit of the present invention.

The presently disclosed embodiments are therefore to be considered in all respects as illustrative and not restrictive, the scope of the invention being indicated solely and exclusively by the appended claims, rather than the foregoing description, and all changes which come within the meaning and range of equivalency of the claims are therefore intended to be embraced therein.

What is claimed is:

1. An analyte sensor for implantation in a body for use with a slotted needle, the sensor comprising:
    a substrate with notches cut in the substrate to form a necked down region in the substrate and a non-necked down region in the substrate wherein the non-necked down region is distal to the notch which forms the necked down region and is for placement within the body; and
    at least one sensor electrode formed from one or more conductive layers,
    wherein the notches creating the necked down region allow the substrate to slide into the slotted needle that has a slot narrow enough to permit passage of the necked down region, but prevents the non-necked down region of the substrate from slipping out of the slotted needle, and
    wherein the notches cut in the substrate do not expose any sensor electrode to analytes.

2. The sensor in accordance with claim 1, wherein the thickness of the substrate ranges from approximately $25\mu$ to $350\mu$.

3. The sensor in accordance with claim 1, wherein the thickness of the substrate ranges from $5\mu$ to $750\mu$.

4. The sensor in accordance with claim 1, wherein a width of the substrate in the non-necked down region is sized to fit within a slotted needle having a diameter smaller than 21 gauge.

5. The sensor in accordance with claim 1, wherein a width of the substrate in the non-necked down region is sized to fit within a slotted needle having a diameter smaller than 22 gauge.

6. The sensor in accordance with claim 1, wherein a width of the substrate in the non-necked down region is sized to fit within a slotted needle having a diameter smaller than 23 gauge.

7. The sensor in accordance with claim 1, wherein a width of the substrate in the non-necked down region is sized to fit within a slotted needle having a diameter smaller than 24 gauge.

8. The sensor in accordance wit claim 1, wherein at least one of the at least one sensor electrode is formed on a first surface of the substrate.

9. The sensor in accordance with claim 8, wherein all of the at least one sensor electrode are only formed on the first surface.

10. The sensor in accordance with claim 8, wherein at least another one of the at least one sensor electrodes is formed on a second surface of the substrate.

11. The sensor in accordance with claim 10, wherein a third one of the at least one sensor electrode is a reference electrode configured to contact a skin surface.

12. A sensor set for use with the sensor in accordance with claim 1 comprising:
   a mounting base adapted for mounting onto a patient's skin; and
   an insertion needle carried by the mounting base to protrude from the mounting base ad having at least a portion of the sensor nested within the insertion needle, the insertion needle defining a longitudinally extending slot along one side to permit sliding withdrawal of the insertion needle from the mounting base and the nested portion of the sensor and to accept the necked down region of the substrate.

13. The sensor of claim 1, wherein the notches are cut in the width of the substrate to form the necked down region of the substrate.

14. An analyte sensor system for implantation in a body, the sensor system comprising:
   a slotted needle;
   a substrate with notches cut in the substrate to form a necked down region in the substrate and a non-necked down region in the substrate wherein to non-necked down region is distal to the notch which forms the necked down region and is for placement within the body; and
   at least one sensor electrode formed from one or more conductive layers,
   wherein the notches creating the necked down region allow the substrate to slide into the slotted needle that has a slot narrow enough to permit passage of the necked down region, but prevents the non-necked down region of the substrate from slipping out of the slotted needle, and
   wherein the notches cut in the substrate do not expose any sensor electrode to analytes.

\* \* \* \* \*